United States Patent [19]

Niwa et al.

[11] Patent Number: 4,979,958

[45] Date of Patent: Dec. 25, 1990

[54] ARTIFICIAL STEM FOR FEMUR OF COXA

[75] Inventors: Shigeo Niwa, Aichi; Kazuhiko Sawai, Nagoya; Tomokazu Hattori, Aichi; Yasumasa Matsuda, Seto; Wataru Yagi, Nagoya; Masami Ishii, Toyota; Junichi Mita; Masuo Yamada, both of Kariya, all of Japan

[73] Assignee: Aisin Seiki Kabushiki Kaisha, Kariya, Japan

[21] Appl. No.: 412,307

[22] Filed: Sep. 26, 1989

[30] Foreign Application Priority Data

Sep. 29, 1988 [JP] Japan .................................. 63-244762

[51] Int. Cl.5 ............................................. A61F 2/32
[52] U.S. Cl. ...................................................... 623/23
[58] Field of Search ....................... 623/16, 18, 19, 20, 623/22, 23

[56] References Cited

U.S. PATENT DOCUMENTS

| 4,645,506 | 2/1987 | Link | 623/23 |
| 4,657,551 | 4/1987 | Ecke | 623/23 |
| 4,695,283 | 9/1987 | Aidinger | 623/23 |
| 4,770,660 | 9/1988 | Averill | 623/23 |
| 4,863,474 | 9/1989 | Brown et al. | 623/23 |

Primary Examiner—David J. Isabella
Attorney, Agent, or Firm—Banner, Birch, McKie & Beckett

[57] ABSTRACT

An artificial stem for femur of coxa in a human body comprises a stem element, a head and a neck connecting the both, each side surface of the stem element corresponding to the indise or outside of a human body being formed by a specific curved or straight line respectively, the cross section of the stem element having a specific shape, and scale-like step patterns being formed on both the front and back surfaces, thereby improving the fitness to the femur of a small body person like Japanese, the stability and the anti-twisting strength after insertion.

1 Claim, 5 Drawing Sheets

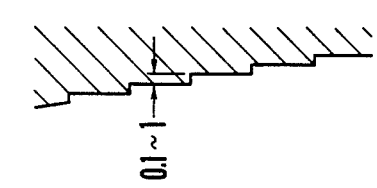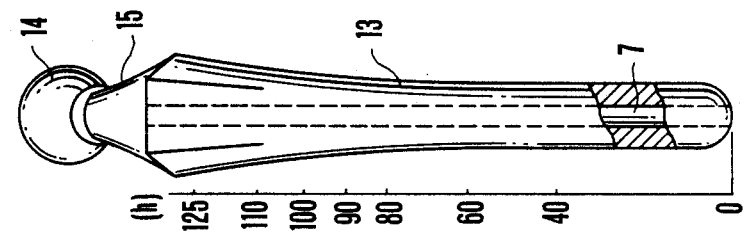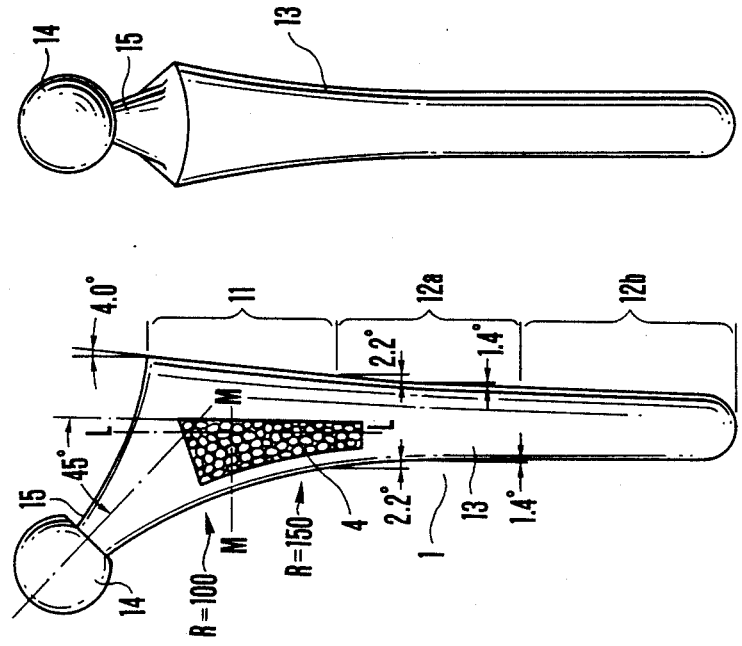

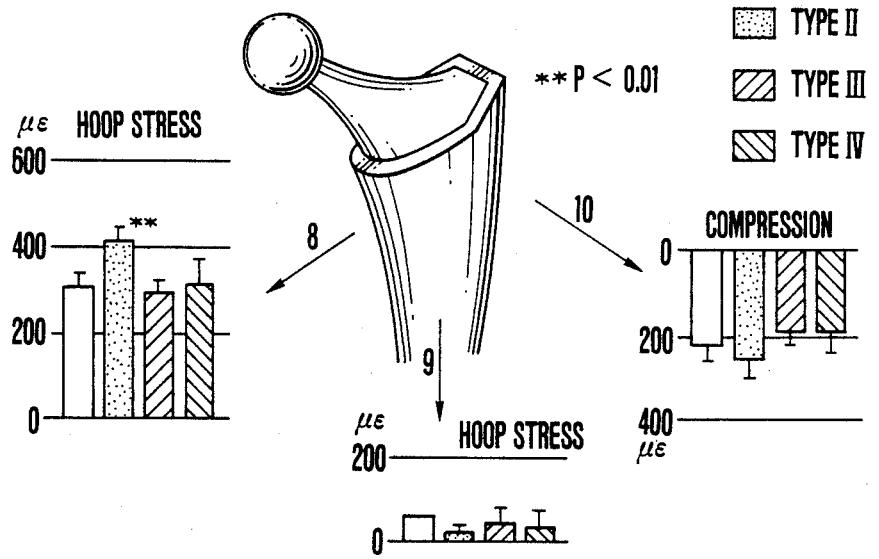
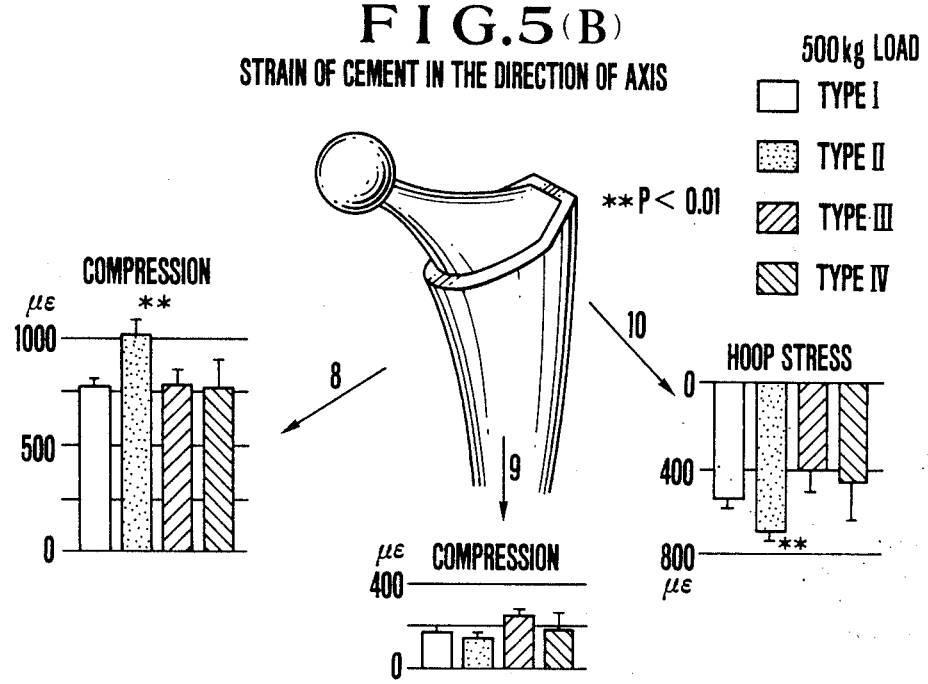

ARTIFICIAL STEM FOR FEMUR OF COXA

BACKGROUND OF THE INVENTION

1. Field of the Invention

This invention relates to an artificial stem for femur of coxa in a human body.

2. Description of the Prior Art

A conventional artificial stem for femus or coxa is disclosed, for example, in Japanese Laid-open Patent Publication No. 41963 of 1985 (Toku-kai-sho 60-41963).

This artificial stem comprises, as shown in FIG. 6(B) (side elevation), a stem element 13 curving slightly backward (leftward in the drawing) in the longitudinal direction of an artificial stem 1, a small head 14 and a neck 15. The stem element 13 comprises an upper proximal portion 11 and a lower distal portion 12. Preferably, the distal portion 12 should be approximately two to three times longer than the proximal portion 11. Numeral 16 designates a shoulder 16. The proximal portion 11 is slightly twisted at an angle of approximately 5 to 15 degrees, as shown in FIG. 6(C). Preferably, the twist should extend throughout the entirety of the proximal portion 11, at an angle of approximately 9 degrees. Also, the proximal portion 11 should preferably be covered with a porous surface 16 to provide good stimulus to the growth of bone.

The proximal portion 11 of the stem elements 13 can be divided, from top to bottom, a proximal, a middle and a distal section. The distal section has a lateral flare that becomes wedge-interlocked with the femur when the stem element 13 is inserted.

The neck 15 diagonally extends upward from the upper proximal section of the proximal portion 11, with the axis thereof forming an angle of approximately 45 degrees with the axis of the stem element 13. The small head 14 is fastened to the neck 15 by taper driving.

The artificial stem for femur of coxa of the above-described type has the following problems:

(1) Designed to fit the femur and medullary cavity of big-body people the artificial stem does not always fit those of small-body people. With the small-body people, therefore, the above artifical stem does not seem to occupy as much space in the bone cavity as is described in the specification.

(2) For the reason described above in (1), it is doubtful if the artificial stem fits in the center of the bond cavity when the stem is set in portion. If it does not fit properly, the thickness of the cement may vary greatly in some places. When a load is placed on the artificial stem, localized stress concentration may result to cause loosening.

The curvature of the stem not fitting the bone cavity of small-bodied people necessitates an additional process of enlarging the insertion hole with file or the like.

(3) The cross-sectional shape of the stem is not always rigid enough to withstand the torsion under a load (like a twist).

(4) The lateral flare may have a wedging effect, it also creates a localized stress concentration that, in turn, can lead to loosening or damages to the bone.

BRIEF SUMMARY OF THE INVENTION

The object of this invention is to provide an artificial stem for femur of coxa that fits to the bone cavity of small-body people like the Japanese, assures easy operation and reduces the possibility of failure.

An artificial stem for femur of coxa according to the present invention comprises an implantable prosthesis for implantation into a femur, comprising an elongated stem element, a neck connected to the upper or proximal end of the stem element and a small joint head fastened to the other end of the neck;

said stem element comprising a proximal portion adjoining the neck, a middle portion below the proximal portion and a distal portion constituting the lowermost part of the stem element; and further including an inside or medial face of the said stem element corresponding to the inside of a human body being defined, in a portion leading from the neck to the proximal portion, by a curve combining an arc having a diameter of 80 to 120 mm and an arc having a diameter of 130 to 170 mm; in a portion leading from the middle portion to the distal portion, by being tapered in two steps at an angle to the center axis of the stem of not greater than 3 degrees and at an angle of not greater than 2 degrees; and in the distal portion, by extending straight;

an outside or lateral face of the stem element corresponding to the outside of a human body, being tapered at an angle to the center axis of the stem of 3 to 5 degrees in the proximal portion, being tapered in two steps at an angle of not greater than 3 degrees and at an angle of not greater than 2 degrees in a portion leading from the middle portion to the distal portion, and extending straight in the distal portion;

the proximal portion having a cross section shaped like an isosceles triangle, with every vertex rounded, the two rounded vertexes forming the base angles of the triangle being chamfered by a straight line, and the two inner sides faces of the triangle being gently sunken;

the middle portion haing a cross section shaped like a triangle with every vertex rounded;

the distal portion having a circular cross section with a diameter of 10 to 18 mm; and the proximal portion having a scale-like stepped pattern raised to a height of $100\mu$ to 1 mm formed along the gently sunken surface on the front or anterior and back or posterior side surfaces thereof.

The artificial stem for femur of coxa according to this invention adapted to be inserted in a bone cavity and fastened with cement has the following functional features;

(1) The artificial stem can readily fit in a bone cavity in the femur of the small-body people because of the affinity in shape attained through careful design consideration.

(2) The proximal and middle portions having cross sections shaped by a combination of an isosceles triangle and arcs have high enough resistance to withstand torsional stress.

(3) The scale-like steps on the gently sunken slope on the proximal portion prevent localized stress concentration, thereby inhibiting the occurrence of loosening and other troubles.

Because of the notable features described above, the artificial stem of this invention can produce the following remarkable effects:

(1) Based on the bone cavity profile data collected from about 50 patients, the artificial stem of this invention is designed to occupy a greater space than conventional stems in the cavity, reducing the space occupied by cement. This, in turn, increases the pressure working on the cement, facilitating the infiltration of the cement into the porous portion of a bone and, as a consequence, fastening the cement and artificial stem more firmly to the bone.

(2) As the stem is designed to attain a uniform distribution of cement therearound, the stress working on the cement is equalized to preclude the breaking of the cement and the resulting loosening of the stem due to stress concentration.

(3) The hollowed surface and scale-like steps in the proximal portion increase the resistance to torsional stress and avoid the concentration of stress on the cement.

(4) The neck whose smallest diameter is 0.4 times the largest diameter of the small head increases the area in which the joint can move.

The foregoing and other objects, features and advantages of the present invention will be understood more clearly and fully from the following detailed description of preferred embodiments with reference to the attached drawings.

BRIEF DESCRIPTION OF THE DRAWINGS

FIGS. 1(A) through 1(E) show a preferred embodiment of this invention, FIG. 1(A) being a front view, FIG. 1(B) being a side elevation showing the left side of FIG. 1(A), FIG. 1(C) being a side elevation showing the right side of FIG. 1(A), FIG. 1(D) being an enlarged cross sectional view of the scale-like steps formed in the proximal portion along the line L—L in FIG. 1(A), and FIG. 1(E) being an enlarged cross sectional view of the hollowed portion in the proximal portion along the line M—M in FIG. 1(A).

FIGS. 5(A) and 5(B) show the strains built up in the cement layer under a load measured by providing grooves of different profiles in the proximal portion.

DETAILED DESCRIPTION OF THE PREFERRED EMBODIMENT

Figure 2:
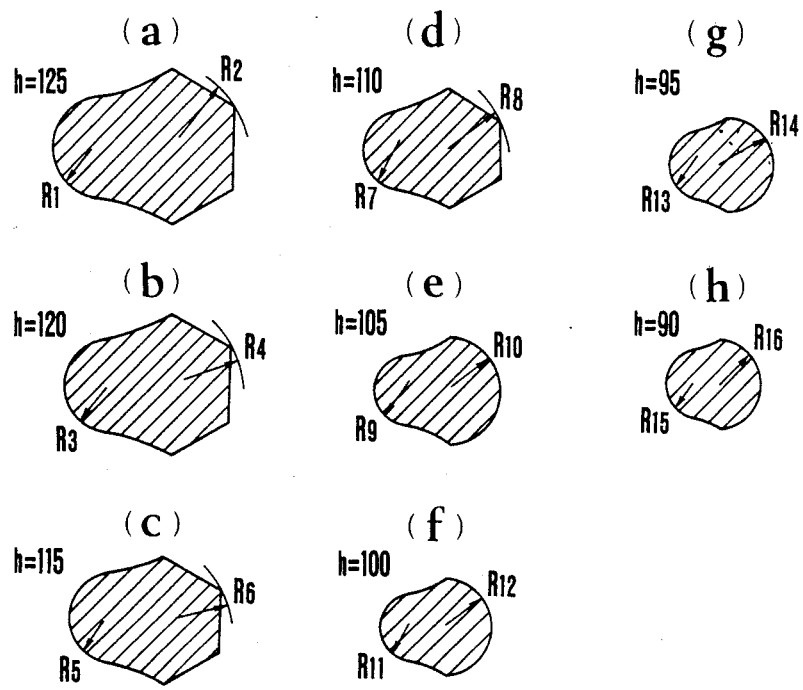
FIGS. 2(a) to (h) show the cross-sections of the proximal portion of the same preferred embodiment.

Now a preferred embodiment of this invention will be described by reference to the accompanying drawings.

An artificial stem 1 shown in FIG. 1 is of medium size. The material can be chosen from among titanium alloy, cobalt-chromium-molybdenum alloy, stainless steel of type SUS 316L and the like. The artificial stem 1 comprises a stem element 13 which, in turn, comprises a proximal portion 11, a middle portion 12a and a distal portion 12b. While a neck 15 is connected to the proximal portion 11, a small head 14 is fastened to the neck 15.

As seen on the left side (corresponding to the inside of a human body) of a front view of in FIG. 1(A), the profile leading from the neck to the proximal portion is defined by two arcs having different radii of curvature of R100 and R150. While the side profile of the middle portion 12a is tapered at an angle of approximately 3 degrees, the distal portion 12b extends straight.

The figures mentioned above are based on the profiles of the bone cavity determined by computerized axial tomography taken from about 50 femurs of Japanese patients suffering from terminal osteoarthritis.

On the right side (corresponding to the outside of a human body) of the front view, the proximal portion 11 and the middle portion 12a are tapered at an angle of approximately 4 degrees and 3 degrees, whereas the distal portion 12b extends straight.

FIG. 2 shows the cross sections at points h=40 to 125 shown in FIG. 1(C).

Each cross section is shaped substantially like an isosceles triangle, with every vertex rounded. The two rounded vertexes forming the base angles of the triangle are chamfered by a straight line. The two sides (corresponding to the inside of a human body) of the triangle are gently sunken. The distal portion 12b has a substantially circular cross section with a diameter of 14 mm. The values of $R_1$ to $R_{16}$ should preferably be as follows: $R_1=8.0$, $R_2=13$, $R_3=7.8$, $R_4=12$, $R_5=7.5$, $R_6=11$, $R_7=7.0$, $R_8=10.2$, $R_9=6.5$, $R_{10}=9.5$, $R_{11}=6.2$, $R_{12}=8.9$, $R_{13}=6.0$, $R_{14}=8.4$, $R_{15}=6.0$ and $R_{16}=8.0$. A stem shaped with these cross sections has a much higher resistance to torsional stress than conventional.

Figure 3:
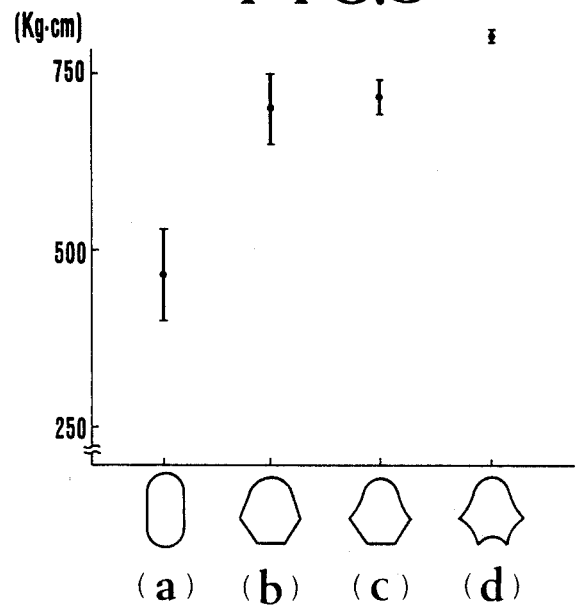
FIG. 3 shows the torsional breaking strength of the artificial bone heads having the cross sections shown at (a) to (d).
Figure 4:
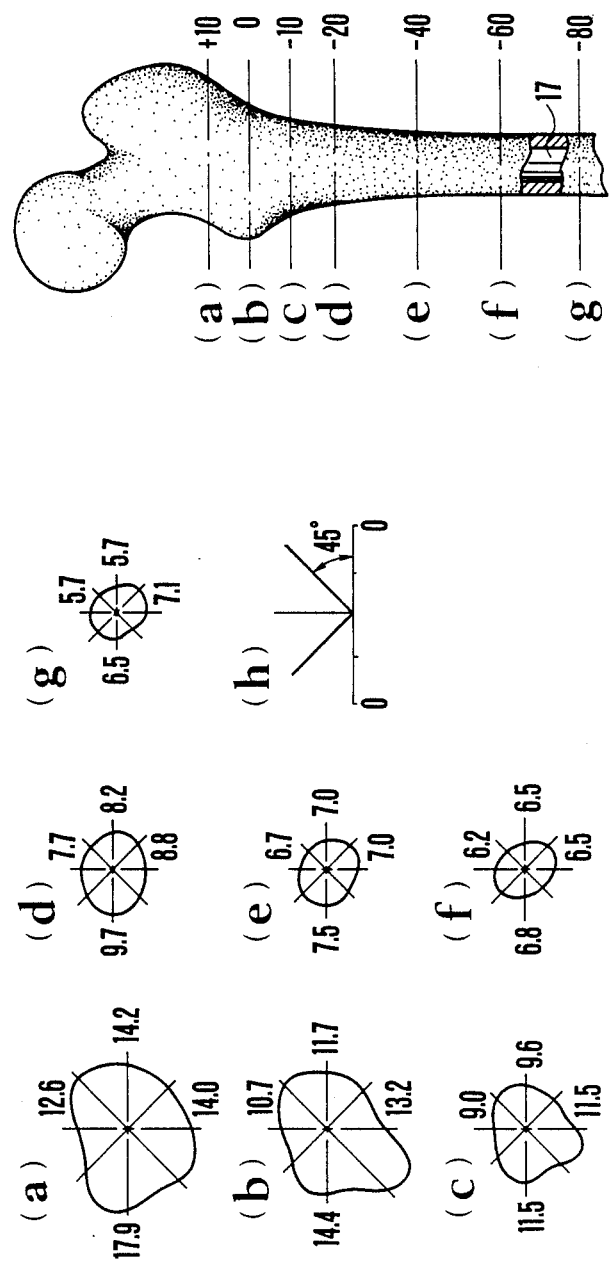
FIGS. 4(a) to (h) shows the cross-sections of a bone cavity.
Figure 6A:
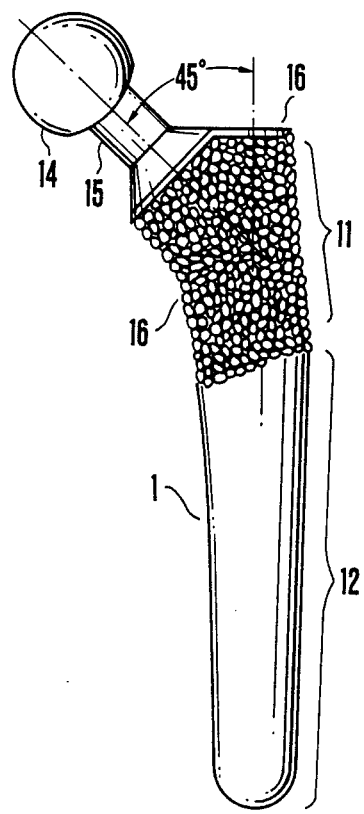
FIGS. 6(A), (B) and (C) show an example of a conventional artificial stem.
Figure 6B:
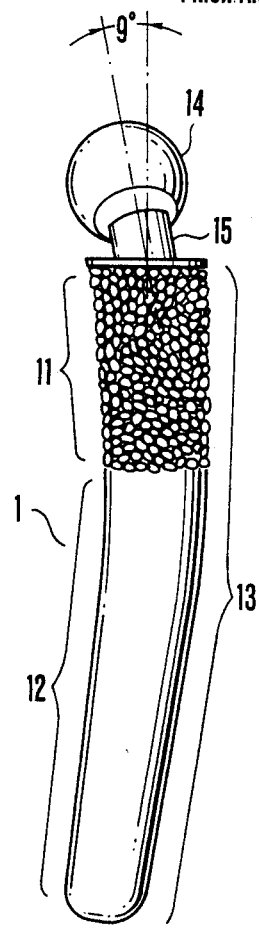
Figure 6C:
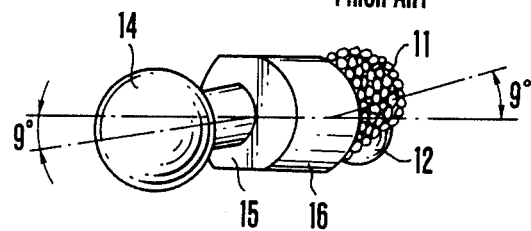

In FIG. 3, the comparison of the torsional breaking strength of stems having different cross sections as shown at (a) to (d) are shown. Obviously, one having an irregularly pentagonal cross section excels.

Scale-like stepped patterns 4a are formed on the hollowed surface in the above two sides (corresponding to the inside of a human body) of the proximal portion 11, as shown in enlarged cross-sectional views of FIGS. 1(D) and (E).

FIGS. 5(A) and 5(B) show the tensile (indicated by arrows 8 and 9) and compressive strains (indicated by an arrow 10) built up in the cement layer when grooves of different profiles are formed on the surface of the proximal portion (type 1 had no groove, type 2 had horizontal grooves on both the inner and outer side surfaces, type 3 had horizontal grooves on both the front and back side surfaces, and type 4 had vertical grooves on the front and back side surfaces). The strains were relatively low with type 3 and 4. Based on this finding, the scale-like stepped pattern was designed by combining the two types that proved effective.

As shown in FIG. 1(A), the axis of the neck 15 extending from the proximal portion 11 has an inclination of approximately 45 degrees to the axis of the stem. The small head 14 (with a diameter of 22 mm) is press-fitted to the tapered neck.

The diameter of the neck is 8.8 mm, which is approximately 0.4 times the diameter of the small head, to enable the joint to move in a large area.

A through hole 7 of approximately 4 mm in diameter should preferably provided along the longitudinal center axis of the artificial stem, as shown in FIG. 1(C), leading from the bottom end of the distal portion 12b to the top end of the proximal portion 11.

It should be understood that, although the preferred embodiment of the present invention has been described herein in considerable detail, certain modifications, changes, and adaptations may be made by those skilled in the art and that it is hereby intended to cover all modifications, changes and adaptations thereof falling within the scope of the appended claim.

What is claimed is:

1. An implantable prosthesis for implantation into a femur comprising:
   an elongated stem having a longitudinal axis and proximal and distal ends;
   a neck element having one end connected to the proximal end of the stem;

a joint head means fastened to the other end of said neck element; and said stem further including anterior, posterior, medial and lateral surfaces and having a proximal portion of the stem adjacent to the proximal end of the stem, a distal portion adjacent to the distal end of the stem and a middle portion between the proximal and distal portions, wherein;

the medial surface of the stem in the proximal portion thereof defines a curve described by, in combination, two successive arcs, a first arc having a diameter of from 80 to 120 mm and a second arc having a diameter of from 130 to 170 mm, respectively; and the medial surface of the stem in the middle portion being tapered from the proximal portion to the distal portion in two steps, wherein the medial surface tapers first at an angle to the longitudinal axis of the stem of not greater than 3 degrees and second at an angle to the longitudinal axis of the stem of not greater than 2 degrees; and the medial surface of the distal portion being straight; and the lateral surface of the stem in the proximal portion being tapered at an angle to the longitudinal axis of the stem of 3 to 5 degrees; and the lateral surface of the stem in the middle portion tapered from the proximal portion to the distal portion in two steps wherein the lateral surface tapers first at an angle to the longitudinal axis of the stem of not greater than 3 degrees and second at an angle to the longitudinal axis of the stem of not greater than 2 degrees; and the lateral surface of the distal portion being straight; and the proximal portion having a cross-section shaped substantially like an isosceles triangle, with each vertex being rounded, and wherein the two vertexes which form the base of the triangle are chamfered by a straight line and the anterior and posterior surfaces being gently sunken and having a scaled pattern of steps formed along the sunken surfaces wherein each of the steps is raised to a height of 100 microns to 1 mm; and the middle portion having a cross-section shaped substantially like an isosceles triangle with each vertex being rounded; and the distal portion having a circular cross-section with a diameter of 10–18 mm.

* * * * *